United States Patent [19]

Saliaris

[11] 4,053,135
[45] Oct. 11, 1977

[54] HOSE CLAMP

[75] Inventor: George P. Saliaris, Worthing, Ohio

[73] Assignee: Sigma Scientific Development, Inc., Columbus, Ohio

[21] Appl. No.: 724,755

[22] Filed: Sept. 20, 1976

[51] Int. Cl.² .............................................. F16K 7/06
[52] U.S. Cl. .................................. 251/10; 24/129 R; 24/132 R; 24/249 R
[58] Field of Search ............... 251/4, 9, 10; 24/129 R, 24/132 R, 132 AC, 249 SL, 255 SL, 257 R

[56] References Cited

U.S. PATENT DOCUMENTS

| 1,361,770 | 12/1920 | O'Connor | 251/10 |
| 3,419,245 | 12/1968 | Scola | 251/10 |
| 3,822,052 | 7/1974 | Lange | 251/10 |

Primary Examiner—Alan Cohan
Assistant Examiner—Richard Gerard
Attorney, Agent, or Firm—Hopgood, Calimafde, Kalil, Blaustein & Lieberman

[57] ABSTRACT

The invention contemplates a single-piece injection-molded plastic hose clamp which may be made, shipped and stored flat and yet which, in assembly to a flexible hose may be applied to squeeze and effectively shut off flow through the hose in a one-handed shut-off operation wherein the shut-off condition is releasably locked. A hinged locking member on one arm of the clamp includes a bracket which, in reaction to the squeezing action to set the clamp, operates as a bellcrank to elevate the locking member to position for automatic resiliently loaded self-latching engagement with a coacting locking member on the other arm of the clamp.

10 Claims, 7 Drawing Figures

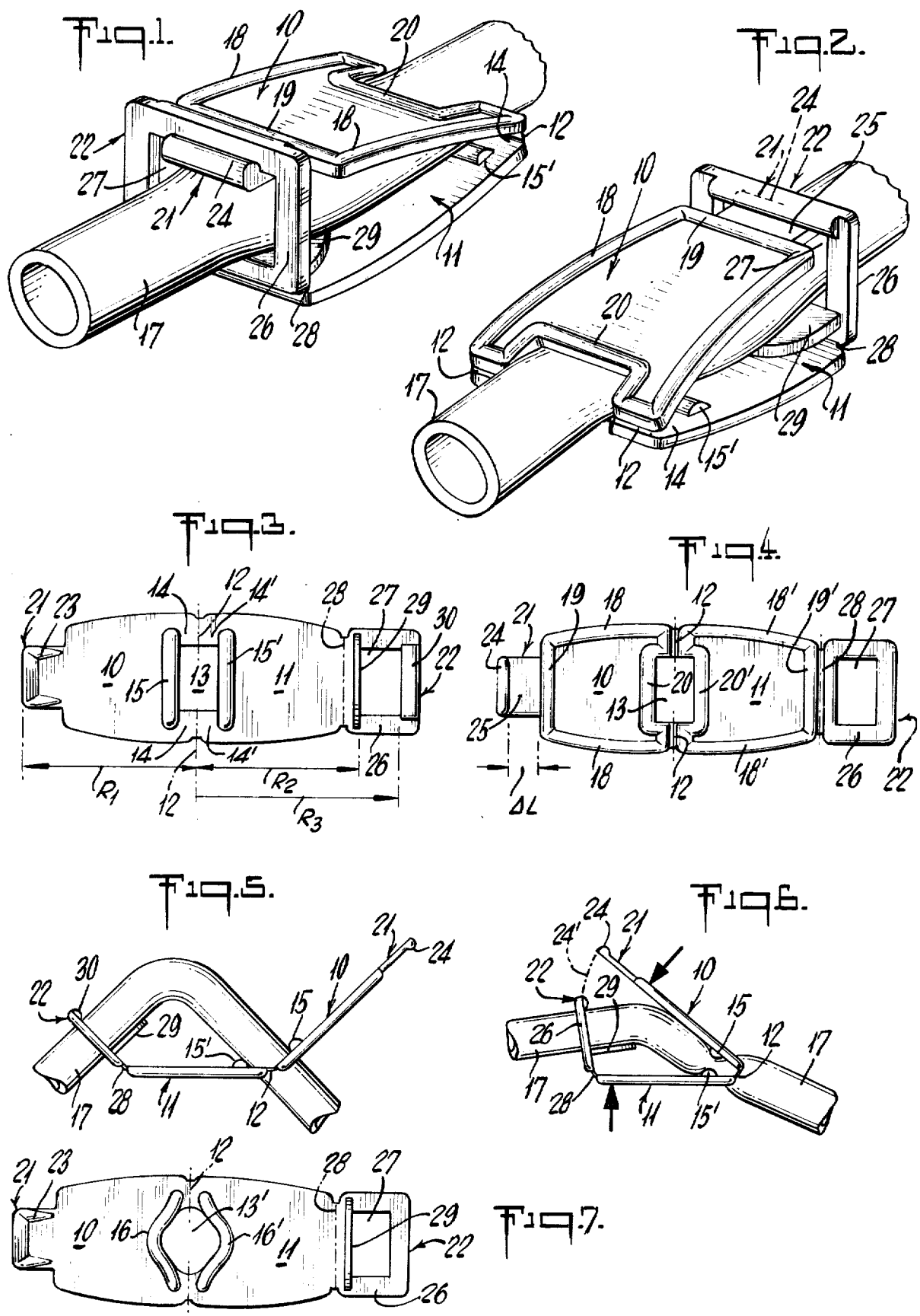

HOSE CLAMP

This invention relates to a releasable hose clamp, of the variety as used for example in hospitals, for irrigation, intravenous-feeding and the like operations.

Hose clamps of the character indicated have traditionally been formed of relatively stiff metal and, of necessity, have had to be shaped into their ultimately usable bent form. Metal-fabrication costs have become a substantial factor, especially in view of today's hospital practice of providing all supporting hardware, such as hoses, clamps, drinking cups, thermometers and the like, uniquely for each patient, to be discarded when the patient leaves. Such practices may be highly sanitary, and they may save the cost of personnel who previously would reclaim, clean and store such articles, but they magnify the significance of unit-cost of the article, and they call for management of larger inventories within minimum space.

Accordingly, it is an object of the invention to provide an improved hose-clamp construction of the character indicated.

Another object is to provide a hose-clamp construction which lends itself economically to the throw-away practice of today, without sacrifice of hose shut-off capability, and with the convenience of one-hand operation.

A general object is to achieve the above objects with a structure of inherently reduced cost, inherently reduced unit storage volume, and inherently simple configuration and operation.

Other objects and various further features of novelty and invention will be pointed out or will occur to those skilled in the art from a reading of the following specification, in conjunction with the accompanying drawings. In said drawings, which show, for illustrative purposes only, preferred forms of the invention:

FIG. 1 is a perspective view of a clamp of the invention set in locked position upon a length of flexible tubing;

FIG. 2 is a view similar to FIG. 1 but from a different aspect;

FIG. 3 is a plan view of the inner surfaces and features of the clamp of FIG. 1, as formed, and as available for shipment and storage, in readiness for use;

FIG. 4 is a plan view of the outer surface features of the clamp of FIG. 1, being the surface opposed to that of FIG. 3;

FIG. 5 is a view in side elevation to illustrate the clamp of FIG. 1, in initial assembly to the flexible tubing, i.e., prior to setting the clamp to pinch-off flow in the tubing;

FIG. 6 is a view as in FIG. 5, taken at a time while the clamp is being set but is short of its set position; and FIG. 7 is a view similar to FIG. 3 to illustrate a modification.

The clamp illustrated in FIGS. 1 to 6 is a single-piece unitary article that is preferably injection-molded of suitable plastic, such as polypropylene. It is formed in the generally flat condition depicted in FIGS. 3 and 4, and it may remain in this condition for shipment and storage, as desired.

The body of the clamp comprises first and second arm panels 10-11, of such body thickness and contour as to achieve relative stiff bending compliance, and with a locally reduced thickness at a flexible interconnection 12, along a central transverse alignment which will be referred to as a central hinge-axis region, at 12. A rectangular opening 13 is provided at the central hinge-axis region of both panels 10-11, limiting hinged interconnection to spaced connected legs 14-14'. On the inner surface of panels 10-11 (FIG. 3), pinch ribs or ridges 15-15' project upward and extend transversely at adjacent margins of the opening 13; these ribs 15-15' are at equal offsets from the hinge-axis region 12, for registry of their pinch action upon a length of flexible hose 17 (e.g., standard polyvinyl tubing) to be clamped. A preference is indicated for a rectangular opening 13 as shown, wherein the longer sides extend transversely, thus permitting the pinch ribs to be located relatively close to the hinge-axis region 12, for enhanced mechanical advantage of hinge application.

Arm panels 10-11 are stiffened against bending by provision of a continuous bead or ribbed formation along the effective perimeter of the outer surface (FIG. 4) of the clamp. In the case of panel 10, this ribbing comprises side courses 18 conforming to the bowed and tapering sides of the panel, an outer transverse course 19, and an inner transverse course 20 which conforms to the margins of opening 13 and to the hinge regions of legs 14. Preferably, the pinch rib 15 (FIG. 3) and the substantial length of the reinforcing course 20 (FIG. 4) are in register, i.e., at equal offsets from the hinge-axis region, for greatest reinforcement at the pinch region. Corresponding reinforcements on the panel 11 are identified with primed notation.

The remainder of the clamp comprises locking formations 21-22 carried at the respective outer longitudinal ends of panels 10-11. The formation 21 is a locking tab, being a narrowed but relatively stiff extension of panel 10, shown with an inner-surface bead formation 23 (FIG. 3) along its perimeter and with a transverse detent rib or bead 24 (FIG. 4) at the outer end of its outer surface, thereby providing a locking region 25 of length $\Delta L$.

The formation 22 comprises an auxiliary panel, establishing a rectangular frame 26 around a locking aperture 27. Frame 26 and panel 11 are of locally reduced thickness at a flexible interconnection 28, along a transverse alignment which will be referred to as an auxiliary hinge-axis region, at 28. Adjacent the hinge region 28, an upstanding bracket panel 29 is effectively rigid with frame 26; and therefore bracket 29 and frame 26 maintain substantially their substantially 90-degree offset relation, for any upward articulation at the hinge-axis region 28. To complete the structure, a reinforcing rib or bead 30 on the inner-surface side, and along the outer transverse span of frame 26, provides reinforcement to retain a locked setting of the clamp.

For use of the described clamp, a length of flexible hose 17 is inserted through the locking aperture 27, over the bracket 29, and through the central opening 13. Bracket 29 forces initial articulation of frame 26 about hinge-axis region 28, and the necessarily arched section of hose 17 forces initial articulation of panel 10 about hinge-axis region 12. Both articulations are upward, placing the FIG. 4 surface on the outside of the bends and the FIG. 3 formations on the inside of the bends, all as shown in FIG. 5. In this condition, flow is permitted in hose 17, and the setting of a locked shut-off condition is but a one-handed operation. To do this, the arch of hose 17 is lightly pressed toward panel 11 as panel 10 is further articulated about axis 12, producing the relationship depicted in FIG. 6, where clamp and hose are poised for the final locking squeeze, it being noted that the swing arc (suggested by phantom line 24') of the outer limit of tab 21 about axis 12 is poised to intercept the inner surface of the frame 26. In the process of actuation from the FIG. 5 to the FIG. 6 position, pinch ribs 15–15' substantially deform the shut-off region of hose 17, and unnecessary surplus length of hose 17 is forced out via the aperture 27, resulting in a shortened hose span between the hinge-axis regions 12–28. Thereafter, as final-squeeze force is applied to panels 10–11 adjacent the locking region (suggested by heavy arrows), the arch of hose 17 is reduced, and the straightening hose applies a turning moment to bracket 29 and frame 26 alike, in the clockwise direction as seen in FIGS. 5 and 6. Thus, once tab 21 intercepts the backside of frame 26, the latter applies a resiliently loaded force to the outer end of tab 21; and when tab 21 clears frame 26 sufficiently, frame 26 snaps over tab 21 and its locking rib 24, assuring a locked condition wherein frame 26 (now virtually perpendicular to panel 11) retains tab 21 and therefore arm panel 10 in a fully compressed hose-pinching relation to panel 11.

Release of the clamp is again a simple one-handed operation. As initial squeeze is applied (e.g., at the arrows of FIG. 6), a simple finger manipulation will displace frame 26 outward enough to clear tab 21, whereupon arms 10–11 may be released to open in response to the compressional resilient loading stored in the squeezed hose.

The embodiment of FIG. 7 is in all respects as in FIGS. 1 to 7 except that the pinch ribs 16–16' are arched or bowed in matching sweeps and at matching offsets from the central hinge-axis region 12. And for more generous accommodation of an inserted hose, the central opening 13' has been similarly bowed, on at least one of its sides.

The described embodiments will be seen to have achieved all stated objects. Basic simplicity and reliability characterize repeated use of the same article, yet it is sufficiently inexpensive to be dispensed with after each use or after each patient has completed his hospital stay.

While the invention has been described in detail for the preferred forms shown, it will be understood that modifications may be made without departure from the claimed scope of the invention.

What is claimed is:

1. A unitary single-piece hose clamp of relatively stiffly compliant material, comprising first and second panels centrally interconnected at a locally relatively weak transverse hinge-axis region, said panels having a hose-admitting opening at their respective transversely central regions; one of said panels having at its opposite end an outwardly projecting auxiliary panel with a locking aperture framed by the outer confines of said auxiliary panel, said one panel being connected to said auxiliary panel at a second locally relatively weak transverse hinge-axis region, and said auxiliary panel aperture being of hose-admitting proportions, an integral bracket member relatively rigidly united to said auxiliary panel adjacent said auxiliary panel hinge-axis region and extending normal to the general plane of said framed aperture; the other of said panels having at its opposite end an outwardly projecting locking tab of width enterable in said locking aperture and relatively rigidly united to said other panel, said tab extending from said central hinge-axis region a distance greater than the distance of the near side of said locking aperture and less than the distance of the remote side of said locking aperture, said last two distances being taken from said central hinge-axis region when said frame is relatively flat with respect to said other panel; whereby a flexible hose inserted through said opening and aperture and arched over said bracket will by the nature of its stiffness tend to upwardly bend said auxiliary panel about the second hinge axis to a moderately elevated position; and whereby upon flexing said panels about the central hinge axis, the confines of the central opening will compress the hose with substantial mechanical advantage as said locking tab approaches the locking aperture; and further whereby upon subsequent hose-compressing pressure applied by squeezing together the locking ends of said panel, the hose will bear against said bracket to further angularly elevate said locking panel into resiliently loaded end abutment with said locking tab until said locking tab clears the adjacent edge of the locking aperture to permit the final resiliently loaded angular displacement of said auxiliary panel into locked retaining engagement with said tab.

2. The hose clamp of claim 1, wherein said material is a plastic.

3. The hose clamp of claim 2, in which said material is polypropylene.

4. The hose clamp of claim 2, formed as a single injection-molded part.

5. The hose clamp of claim 1, in which adjacent hose-pinching surfaces of said panels each include transversely elongate pinch ribs near the central opening and at corresponding radial offset from the central hinge axis.

6. The hose clamp of claim 5, in which said pinch ribs are straight and parallel to each other.

7. The hose clamp of claim 5, in which said pinch ribs are arched in the direction away from the central hinge axis.

8. The hose clamp of claim 1, in which the outer end of said tab includes at its outer end a locking detent rising above the aperture-engaging surfaces of said tab.

9. The hose clamp of claim 8, in which said locking detent is a transversely extending rib.

10. A hose clamp comprising two arms of relatively stiffly compliant material connected by a bending hinge connection at one end, said arms having a hose-admitting aperture at the hinge connecting region, a bracket member hingedly connected to the other end of one of said arms on a hinge axis substantially parallel to that of said hinge connection, said bracket member having a first bracket panel with a hose-admitting aperture and a second bracket panel substantially normal to said first bracket panel, the bracket hinge axis being near the connection of said panels, said second bracket panel when articulated to lie along the inner surface of said one arm being at least in part overlapped by said second arm when said arms are folded together about said hinge connection, and releasable locking means coacting between said second arm and said first bracket panel to retain a folded position of said arms when squeezed against a length of flexible hose which passes between said arms via said apertures and over said second bracket panel.

* * * * *